US012773188B2

(12) United States Patent
Kitamura

(10) Patent No.: US 12,773,188 B2
(45) Date of Patent: Oct. 27, 2026

(54) IMAGE PROCESSING DEVICE, METHOD, AND PROGRAM

(71) Applicant: FUJIFILM Corporation, Tokyo (JP)

(72) Inventor: Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/306,966

(22) Filed: Apr. 25, 2023

(65) Prior Publication Data

US 2023/0346351 A1 Nov. 2, 2023

(30) Foreign Application Priority Data

May 2, 2022 (JP) ................................ 2022-076306

(51) Int. Cl.
*A61B 8/00* (2006.01)
*A61B 6/00* (2024.01)
(Continued)

(52) U.S. Cl.
CPC ................ *A61B 8/52* (2013.01); *A61B 6/487* (2013.01); *A61B 6/5247* (2013.01); *A61B 8/12* (2013.01);
(Continued)

(58) Field of Classification Search
CPC .. A61B 8/52; A61B 8/13; A61B 6/487; A61B 6/5247; A61B 8/4254; A61B 8/4416; A61B 8/4438; A61B 8/466; A61B 8/483; A61B 8/5261; A61B 8/12; G06T 7/80; G06T 7/97; G06T 2207/10136
See application file for complete search history.

(56) References Cited

U.S. PATENT DOCUMENTS 5,771,895 A * 6/1998 Slager ...................... A61B 8/12
600/467
9,375,164 B2 * 6/2016 Tolkowsky ............. A61B 5/06
(Continued)

FOREIGN PATENT DOCUMENTS

| | | |
|---|---|---|
| JP | 2010522597 | 7/2010 |
| JP | 2010220742 | 10/2010 |
| WO | 2021247744 | 12/2021 |

OTHER PUBLICATIONS

"Search Report of Europe Counterpart Application", issued on Jul. 27, 2023, p. 1-p. 7.

(Continued)

*Primary Examiner* — Adil Partap S Virk
(74) *Attorney, Agent, or Firm* — JCIPRNET

(57) ABSTRACT

A processor sequentially acquires a plurality of radiation images of a subject having a body cavity into which an ultrasonic endoscope to which an ultrasonic imaging device is attached and to which a radiation impermeable marker is attached is inserted, sequentially acquires a plurality of two-dimensional ultrasound images corresponding to the plurality of radiation images, which are acquired by the ultrasonic imaging device, recognizes a position and a posture of the ultrasonic endoscope in the body cavity based on the marker included in each of the plurality of radiation images, and derives a three-dimensional ultrasound image from the plurality of two-dimensional ultrasound images based on the position and the posture of the ultrasonic endoscope recognized with respect to the plurality of radiation images.

4 Claims, 11 Drawing Sheets

(51) Int. Cl.

| | |
|---|---|
| ***A61B 8/12*** | (2006.01) |
| ***A61B 8/13*** | (2006.01) |
| ***G06T 7/00*** | (2017.01) |
| ***G06T 7/80*** | (2017.01) |

(52) U.S. Cl.

CPC .............. *A61B 8/13* (2013.01); *A61B 8/4416* (2013.01); *A61B 8/466* (2013.01); *A61B 8/483* (2013.01); *G06T 7/80* (2017.01); *G06T 7/97* (2017.01); *G06T 2207/10136* (2013.01)

(56) References Cited

U.S. PATENT DOCUMENTS

| | | | | | |
|---|---|---|---|---|---|
| 10,172,582 | B2 * | 1/2019 | Dascal | A61B 8/12 | |
| 10,835,207 | B2 * | 11/2020 | Altmann | A61B 8/4488 | |
| 2004/0097805 | A1 * | 5/2004 | Verard | A61B 34/20 | 600/428 |
| 2004/0147837 | A1 * | 7/2004 | Macaulay | A61B 8/0833 | 600/117 |
| 2005/0033164 | A1 * | 2/2005 | Yatsuo | G01R 33/286 | 600/434 |
| 2005/0101870 | A1 * | 5/2005 | Yamaguchi | A61B 17/2256 | 600/466 |
| 2005/0113685 | A1 * | 5/2005 | Maschke | A61B 5/02007 | 600/467 |
| 2005/0251028 | A1 * | 11/2005 | Boese | A61B 6/503 | 600/425 |
| 2006/0036167 | A1 * | 2/2006 | Shina | A61B 6/12 | 600/433 |
| 2006/0253024 | A1 * | 11/2006 | Altmann | G06T 17/00 | 600/437 |
| 2006/0287595 | A1 * | 12/2006 | Maschke | A61B 8/12 | 604/95.01 |
| 2007/0015996 | A1 * | 1/2007 | Camus | A61B 8/5238 | 600/407 |
| 2007/0043292 | A1 * | 2/2007 | Camus | A61B 8/12 | 600/443 |
| 2007/0167801 | A1 * | 7/2007 | Webler | G06T 19/00 | 600/459 |
| 2007/0255133 | A1 * | 11/2007 | Suhling | A61B 6/463 | 600/425 |
| 2008/0008368 | A1 * | 1/2008 | Matsumoto | G06T 19/00 | 382/128 |
| 2008/0095421 | A1 * | 4/2008 | Sun | A61B 6/5247 | 382/131 |
| 2008/0097150 | A1 * | 4/2008 | Hasegawa | G06T 5/80 | 600/109 |
| 2008/0146932 | A1 * | 6/2008 | Chalana | A61B 8/0866 | 600/447 |
| 2008/0183073 | A1 * | 7/2008 | Higgins | A61B 6/032 | 600/425 |
| 2008/0262342 | A1 | 10/2008 | Averbruch | | |
| 2008/0298660 | A1 * | 12/2008 | Yamagata | G01S 15/899 | 600/437 |
| 2008/0300487 | A1 * | 12/2008 | Govari | A61B 8/0883 | 600/443 |
| 2009/0005679 | A1 * | 1/2009 | Dala-Krishna | G06T 7/80 | 600/437 |
| 2009/0036775 | A1 * | 2/2009 | Ikuma | A61B 8/5238 | 600/443 |
| 2009/0163810 | A1 * | 6/2009 | Kanade | G06T 7/344 | 600/443 |
| 2009/0175518 | A1 * | 7/2009 | Ikuma | A61B 6/032 | 382/128 |
| 2009/0326373 | A1 * | 12/2009 | Boese | G06T 7/38 | 600/440 |
| 2010/0063400 | A1 * | 3/2010 | Hall | A61B 6/4417 | 378/4 |
| 2010/0145197 | A1 * | 6/2010 | Stapf | A61B 8/4488 | 382/128 |
| 2011/0135172 | A1 | 6/2011 | Kitamura | | |
| 2011/0245660 | A1 * | 10/2011 | Miyamoto | G06T 15/08 | 382/128 |
| 2012/0136208 | A1 * | 5/2012 | Itai | G06T 19/003 | 382/128 |
| 2012/0155731 | A1 * | 6/2012 | Weersink | G06T 7/344 | 382/128 |
| 2012/0245458 | A1 * | 9/2012 | Gogin | A61B 6/5247 | 600/424 |
| 2012/0296202 | A1 * | 11/2012 | Mountney | A61B 6/12 | 600/424 |
| 2013/0023766 | A1 | 1/2013 | Han et al. | | |
| 2013/0041252 | A1 * | 2/2013 | Vignon | A61B 8/0841 | 600/443 |
| 2013/0131510 | A1 * | 5/2013 | Toma | A61B 8/483 | 600/437 |
| 2013/0331687 | A1 * | 12/2013 | Liao | A61B 6/12 | 600/424 |
| 2014/0303491 | A1 * | 10/2014 | Shekhar | G06T 7/337 | 600/424 |
| 2015/0193931 | A1 * | 7/2015 | Fuchigami | A61B 8/466 | 382/132 |
| 2015/0223773 | A1 * | 8/2015 | John | A61B 8/0841 | 600/424 |
| 2015/0302634 | A1 * | 10/2015 | Florent | G06T 7/30 | 345/419 |
| 2016/0095573 | A1 * | 4/2016 | Tanaka | A61B 8/5207 | 600/443 |
| 2016/0180521 | A1 * | 6/2016 | Mountney | G06T 5/60 | 382/131 |
| 2016/0183888 | A1 | 6/2016 | Averbruch | | |
| 2017/0032512 | A1 * | 2/2017 | Sun | G06F 18/24 | |
| 2018/0130200 | A1 * | 5/2018 | Miao | A61B 8/4245 | |
| 2018/0158201 | A1 * | 6/2018 | Thompson | A61B 8/12 | |
| 2019/0090951 | A1 * | 3/2019 | Camus | A61B 8/483 | |
| 2019/0099159 | A1 * | 4/2019 | Voigt | G06T 7/60 | |
| 2019/0282190 | A1 * | 9/2019 | Dargis | G06T 11/005 | |
| 2019/0374130 | A1 * | 12/2019 | Bydlon | A61B 10/04 | |
| 2020/0036910 | A1 * | 1/2020 | Alzaga | G06T 7/70 | |
| 2020/0250835 | A1 * | 8/2020 | Alzaga | A61B 5/1114 | |
| 2020/0405397 | A1 * | 12/2020 | Liu | A61B 34/10 | |
| 2021/0137350 | A1 * | 5/2021 | Inglis | A61B 1/00016 | |
| 2022/0022967 | A1 * | 1/2022 | Nijhof | A61B 6/487 | |
| 2022/0292655 | A1 * | 9/2022 | Taniyama | A61B 8/463 | |
| 2025/0221624 | A1 * | 7/2025 | Sakaguchi | A61B 5/0066 | |

OTHER PUBLICATIONS

"Notice of Reasons for Refusal of Japan Counterpart Application", issued on Dec. 2, 2025, with English translation thereof, p. 1-p. 7.

"Decision of Dismissal of Amendment of Japan Counterpart Application", issued on Jun. 30, 2026, with English translation thereof, p. 1-p. 3.

* cited by examiner

IMAGE PROCESSING DEVICE, METHOD, AND PROGRAM

CROSS REFERENCE TO RELATED APPLICATIONS

The present application claims priority from Japanese Patent Application No. 2022-076306, filed on May 2, 2022, the entire disclosure of which is incorporated herein by reference.

BACKGROUND

Technical Field

The present disclosure relates to an image processing device, method, and program.

Related Art

An endoscope is inserted into a lumen such as a bronchus or a digestive organ of a subject, and that an endoscopic image in the lumen is acquired to observe an inside of the lumen. In addition, a biopsy treatment is also performed in which a tissue at a site suspected to be a lesion found in the endoscopic image is collected with a treatment tool such as a forceps attached to a distal end of the endoscope. In a case of performing such a treatment using the endoscope, it is important that the endoscope accurately reaches a target position in the subject. Therefore, a positional relationship between the endoscope and a human body structure is grasped by continuously irradiating the subject with radiation from a radiation source during the treatment and performing fluoroscopic imaging to display the acquired fluoroscopic image in real time. However, it is difficult to grasp a depth inside the subject in the fluoroscopic image. In addition, in a case in which the lesion is small, it may be difficult to see in the endoscopic image, so that a success rate of collecting the tissue of the lesion is reduced.

Therefore, a small ultrasonic observing device is mounted on the distal end of the endoscope, a lesion on an outside of a wall is confirmed by ultrasound from an inside of the bronchus, and a tissue is collected while confirming whether a treatment tool for collecting the tissue contacts the lesion. However, even in a case in which such an endoscope is used, a positional relationship between the treatment tool and the endoscope is confirmed by using the fluoroscopic image, so that it is difficult to collect the tissue with a complete grasp of the positional relationship.

In order to solve such a problem, a marker made of a material that does not transmit radiation is attached to the distal end of the endoscope, and a position and a posture of the endoscope are grasped by using a marker image included in the fluoroscopic image (for example, refer to JP2010-522597A).

In the method disclosed in JP2010-522597A, although it is easy to grasp the position and the posture of the endoscope in the fluoroscopic image, a relationship between a position of the lesion and the position of the endoscope remains unclear.

SUMMARY OF THE INVENTION

The present disclosure has been made in view of the above circumstances, and an object of the present disclosure is to facilitate a grasp of a positional relationship between a distal end of an endoscope and a lesion.

An image processing device according to the present disclosure comprises: at least one processor, in which the processor is configured to: sequentially acquire a plurality of radiation images of a subject having a body cavity into which an ultrasonic endoscope to which an ultrasonic imaging device is attached and to which a radiation impermeable marker is attached is inserted; sequentially acquire a plurality of two-dimensional ultrasound images corresponding to the plurality of radiation images, which are acquired by the ultrasonic imaging device; recognize a position and a posture of the ultrasonic endoscope in the body cavity based on the marker included in each of the plurality of radiation images; and derive a three-dimensional ultrasound image from the plurality of two-dimensional ultrasound images based on the position and the posture of the ultrasonic endoscope recognized with respect to the plurality of radiation images.

In the image processing device according to the present disclosure, the processor may be configured to: perform registration between the radiation image and the three-dimensional ultrasound image; and superimpose and display the registered three-dimensional ultrasound image on the radiation image.

In addition, in the image processing device according to the present disclosure, the processor may be configured to: extract the body cavity into which the ultrasonic endoscope is inserted from a three-dimensional image of the subject acquired in advance; correct the position and the posture of the ultrasonic endoscope according to a shape of the extracted body cavity; and derive a three-dimensional ultrasound image from the plurality of two-dimensional ultrasound images based on the corrected position and posture.

An image processing method according to the present disclosure comprises: sequentially acquiring a plurality of radiation images of a subject having a body cavity into which an ultrasonic endoscope to which an ultrasonic imaging device is attached and to which a radiation impermeable marker is attached is inserted; sequentially acquiring a plurality of two-dimensional ultrasound images corresponding to the plurality of radiation images, which are acquired by the ultrasonic imaging device; recognizing a position and a posture of the ultrasonic endoscope in the body cavity based on the marker included in each of the plurality of radiation images; and deriving a three-dimensional ultrasound image from the plurality of two-dimensional ultrasound images based on the position and the posture of the ultrasonic endoscope recognized with respect to the plurality of radiation images.

An image processing program according to the present disclosure causes a computer to execute a process comprising: sequentially acquiring a plurality of radiation images of a subject having a body cavity into which an ultrasonic endoscope to which an ultrasonic imaging device is attached and to which a radiation impermeable marker is attached is inserted; sequentially acquiring a plurality of two-dimensional ultrasound images corresponding to the plurality of radiation images, which are acquired by the ultrasonic imaging device; recognizing a position and a posture of the ultrasonic endoscope in the body cavity based on the marker included in each of the plurality of radiation images; and deriving a three-dimensional ultrasound image from the plurality of two-dimensional ultrasound images based on the position and the posture of the ultrasonic endoscope recognized with respect to the plurality of radiation images.

According to the present disclosure, it is possible to easily confirm the position of the lesion included in the radiation image by using the three-dimensional ultrasound image.

DETAILED DESCRIPTION

Figure 1:
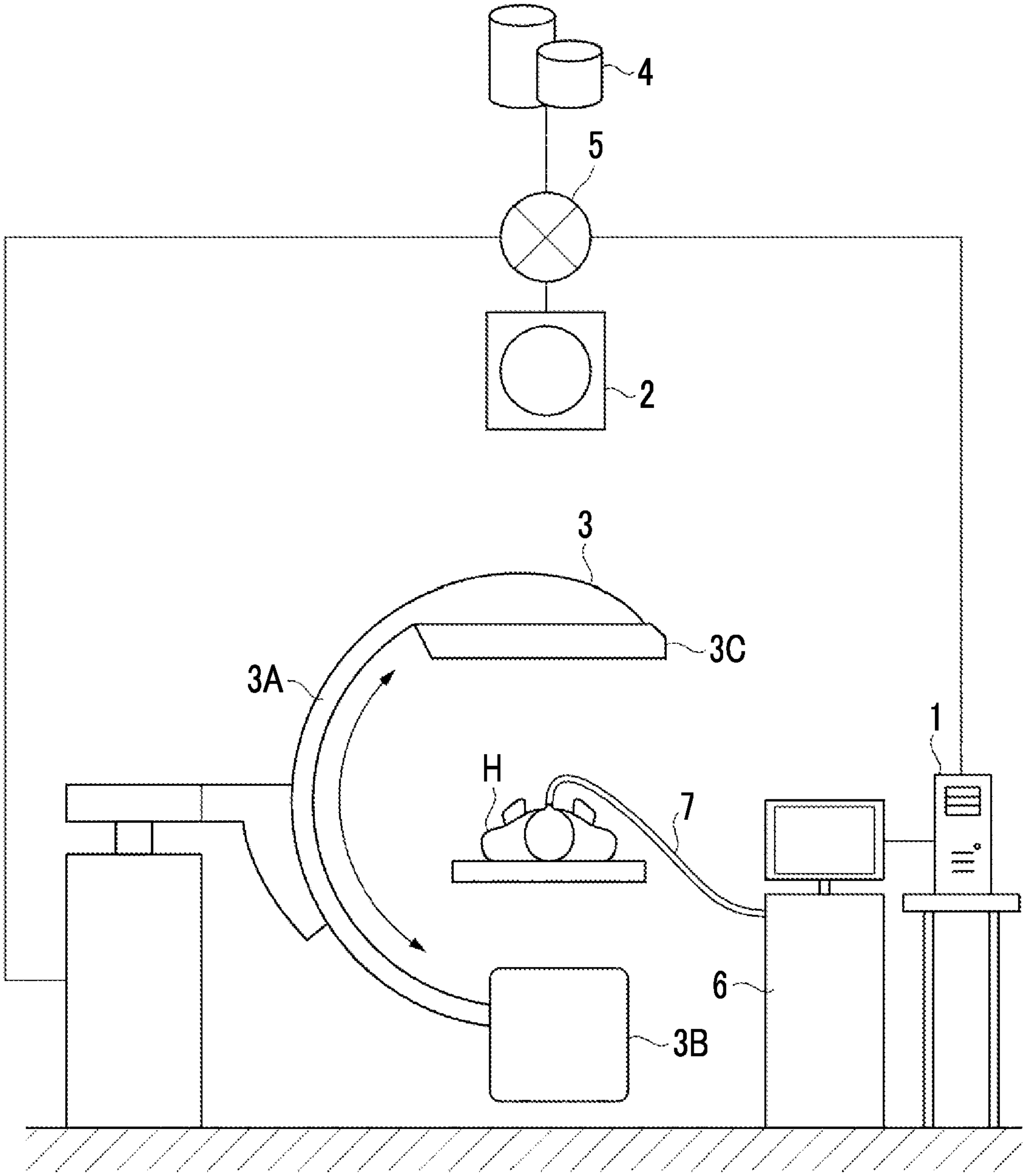
FIG. 1 is a diagram showing a schematic configuration of a medical information system to which an image processing device according to a first embodiment of the present disclosure is applied.

Hereinafter, embodiments of the present disclosure will be described with reference to the drawings. First, a configuration of a medical information system to which an image processing device according to a first embodiment is applied will be described. FIG. 1 is a diagram showing a schematic configuration of the medical information system. In the medical information system shown in FIG. 1, a computer 1 including the image processing device according to the first embodiment, a three-dimensional image pick-up device 2, a fluoroscopic image pick-up device 3, and an image storage server 4 are connected in a communicable state via a network 5.

The computer 1 includes the image processing device according to the first embodiment, and an image processing program of the first embodiment is installed in the computer 1. The computer 1 is installed in a treatment room in which a subject is treated as described below. The computer 1 may be a workstation or a personal computer directly operated by a medical worker who performs a treatment or may be a server computer connected thereto via a network. The image processing program is stored in a storage device of the server computer connected to the network or in a network storage in a state of being accessible from the outside, and is downloaded and installed in the computer 1 used by a doctor in response to a request. Alternatively, the image processing program is distributed by being recorded on a recording medium such as a digital versatile disc (DVD) or a compact disc read only memory (CD-ROM) and is installed on the computer 1 from the recording medium.

The three-dimensional image pick-up device 2 is a device that generates a three-dimensional image representing a treatment target site of a subject H by imaging the site, and is specifically, a CT device, an MRI device, a positron emission tomography (PET) device, and the like. The three-dimensional image including a plurality of tomographic images, which is generated by the three-dimensional image pick-up device 2, is transmitted to and stored in the image storage server 4. In addition, in the present embodiment, the treatment target site of the subject H is a lung, and the three-dimensional image pick-up device 2 is the CT device. A CT image including a chest portion of the subject H is acquired in advance as a three-dimensional image by imaging the chest portion of the subject H before a treatment on the subject H as described below and stored in the image storage server 4.

The fluoroscopic image pick-up device 3 includes a C-arm 3A, an X-ray source 3B, and an X-ray detector 3C. The X-ray source 3B and the X-ray detector 3C are attached to both end parts of the C-arm 3A, respectively. In the fluoroscopic image pick-up device 3, the C-arm 3A is configured to be rotatable and movable such that the subject H can be imaged from any direction. As will be described below, the fluoroscopic image pick-up device 3 sequentially acquires X-ray images of the subject H by performing fluoroscopic imaging in which the subject H is continuously irradiated with X-rays at a predetermined frame rate during the treatment on the subject H, and the X-rays transmitted through the subject H are sequentially detected by the X-ray detector 3C. In the following description, the X-ray images that are sequentially acquired will be referred to as fluoroscopic images. The fluoroscopic image is an example of a radiation image according to the present disclosure. In addition, the X-ray is an example of radiation according to the present disclosure.

The image storage server 4 is a computer that stores and manages various types of data, and comprises a large-capacity external storage device and database management software. The image storage server 4 communicates with another device via the wired or wireless network 5 and transmits and receives image data and the like. Specifically, various types of data including image data of the three-dimensional image acquired by the three-dimensional image pick-up device 2, the fluoroscopic image acquired by the fluoroscopic image pick-up device 3, and an ultrasound image acquired by an ultrasonic endoscope device 6 which will be described below are acquired via the network, and managed by being stored in a recording medium such as a large-capacity external storage device. A storage format of the image data and the communication between the respective devices via the network 5 are based on a protocol such as digital imaging and communication in medicine (DICOM).

In the present embodiment, it is assumed that a biopsy treatment is performed in which while performing fluoroscopic imaging of the subject H, a part of a lesion such as a pulmonary nodule existing in the lung of the subject H is collected to examine the presence or absence of a disease in detail. For this reason, the fluoroscopic image pick-up device 3 is disposed in a treatment room for performing a biopsy. In addition, the ultrasonic endoscope device 6 is installed in the treatment room. The ultrasonic endoscope device 6 comprises an endoscope 7 whose distal end is attached with a treatment tool such as an ultrasound probe and a puncture needle.

Figure 2:
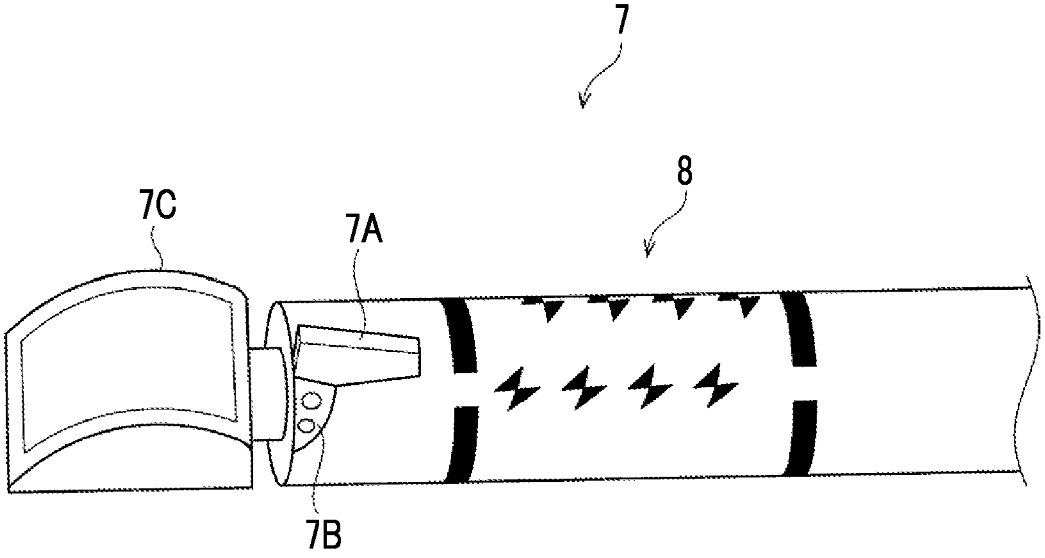
FIG. 2 is a diagram showing a distal end portion of an endoscope according to the present embodiment.

FIG. 2 is a diagram showing a distal end portion of the endoscope 7 according to the present embodiment. As shown in FIG. 2, a channel 7A through which a treatment tool (not shown) such as a puncture needle enters and exits is formed at the distal end of the endoscope 7, and an optical system 7B for acquiring an endoscopic image is attached in the vicinity of an outlet of the channel 7A. Further, an ultrasound probe 7C is attached at a position on a distal end side with respect to the channel 7A. In addition, a radiation impermeable marker 8 is attached to the distal end of the endoscope 7. The ultrasonic endoscope device 6 acquires an ultrasound image of a cross section orthogonal to a major axis of the endoscope 7 in a direction in which the ultrasound probe 7C is directed. A range in which the ultrasound image can be picked up is a predetermined trapezoidal range in which the ultrasonic wave spreads from the ultrasound probe 7C.

Figure 3:
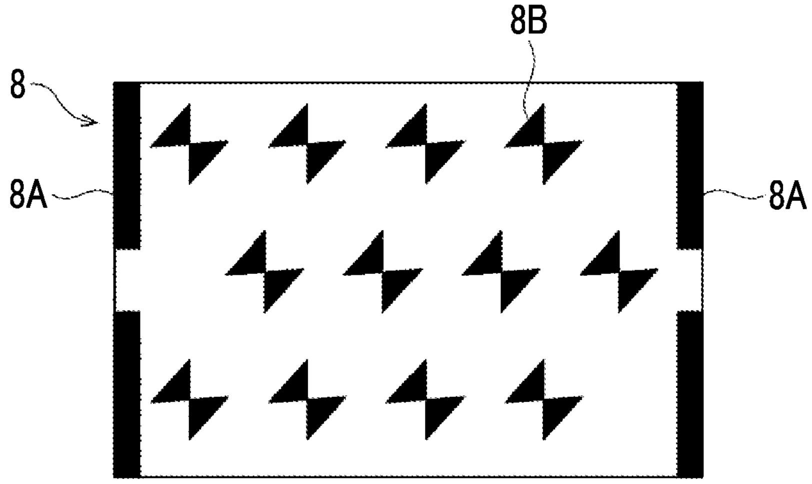
FIG. 3 is a development view of a radiation impermeable marker.
Figure 4:
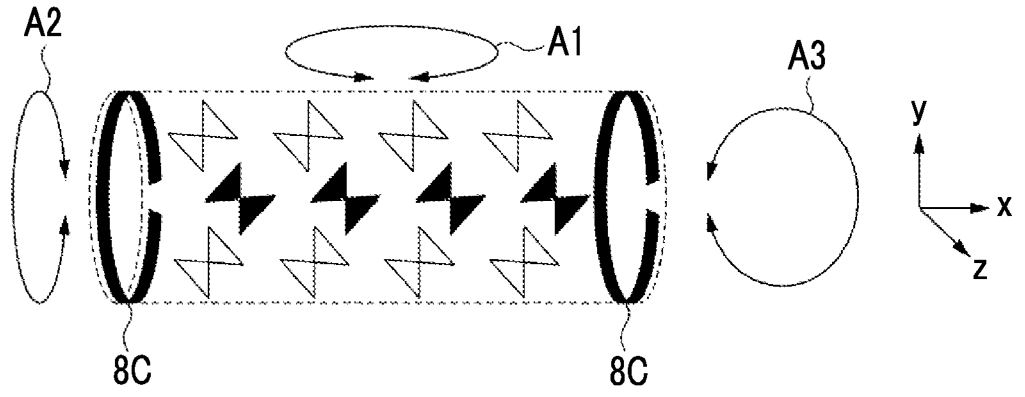
FIG. 4 is a diagram showing a state in which the radiation impermeable marker is attached.

FIG. 3 is a development view of the radiation impermeable marker. As shown in FIG. 3, the radiation impermeable marker 8 includes a linear marker 8A and a chess board marker 8B. Such a marker 8 is attached such that the marker 8 is wound around the distal end of the endoscope 7, whereby, as shown in FIG. 4, the linear marker 8A becomes an annular marker 8C with a part cut out. In FIG. 4, the outline chess board marker 8B indicates a backward-facing state.

In the present embodiment, in order to perform a biopsy of the lesion, an operator inserts the endoscope 7 into the bronchus of the subject H, picks up a fluoroscopic image of the subject H with the fluoroscopic image pick-up device 3, confirms a distal end position of the endoscope 7 in the subject H in the fluoroscopic image while displaying the picked-up fluoroscopic image in real time, and moves the distal end of the endoscope 7 to a target position of the lesion.

Here, lung lesions such as pulmonary nodules occur outside the bronchus rather than inside the bronchus. Therefore, after moving the distal end of the endoscope 7 to the target position, the operator picks up an ultrasound image from an inner surface to the outside of the bronchus with the ultrasound probe, displays the ultrasound image, and performs treatment of collecting a part of the lesion using a treatment tool while confirming a position of the lesion in the ultrasound image.

In this case, a position and a posture of the distal end of the endoscope 7 can be recognized by an appearance of the marker 8 attached to the distal end of the endoscope 7 in the fluoroscopic image. Regarding the posture, in a case in which three axes are spatially set as shown in FIG. 4, the annular marker 8C changes as shown in "around y-axis" in an upper row of FIG. 5 because of a change in posture caused by rotation of the distal end of the endoscope 7 around a y-axis (that is, in a direction of arrow A1). In addition, the annular marker 8C changes as shown in "around x-axis" in a middle row of FIG. 5 because of a change in posture caused by rotation of the distal end of the endoscope 7 around an x-axis (that is, in a direction of arrow A2). In addition, the annular marker 8C changes as shown in "around z-axis" in a lower row of FIG. 5 because of a change in posture caused by rotation of the distal end of the endoscope 7 around a z-axis (that is, in a direction of arrow A3). The posture of the distal end of the endoscope 7 can be recognized more accurately by using the chess board marker 8B as an auxiliary.

Therefore, in a case of picking up an ultrasound image, the operator can determine the position and the posture of the distal end of the endoscope 7 in a state in which the lesion is included in the ultrasound image by a position and a shape of the marker 8 included in the fluoroscopic image, and can reliably collect the lesion by making the treatment tool reach the lesion while maintaining the position of the distal end.

On the other hand, in a case in which an ultrasonic endoscope on which the treatment tool is not mounted is used, after confirming the position of the lesion, an endoscope on which the treatment tool is mounted is inserted to the subject to collect the lesion tissue. In this case, in a case in which the same marker 8 is also attached to the endoscope on which the treatment tool is mounted, the operator can easily remember the position of the lesion by relying on the marker 8 included in the fluoroscopic image, so that the endoscope on which the treatment tool is mounted can be inserted into the position of the lesion and the tissue of the lesion can be reliably collected.

Figure 6:
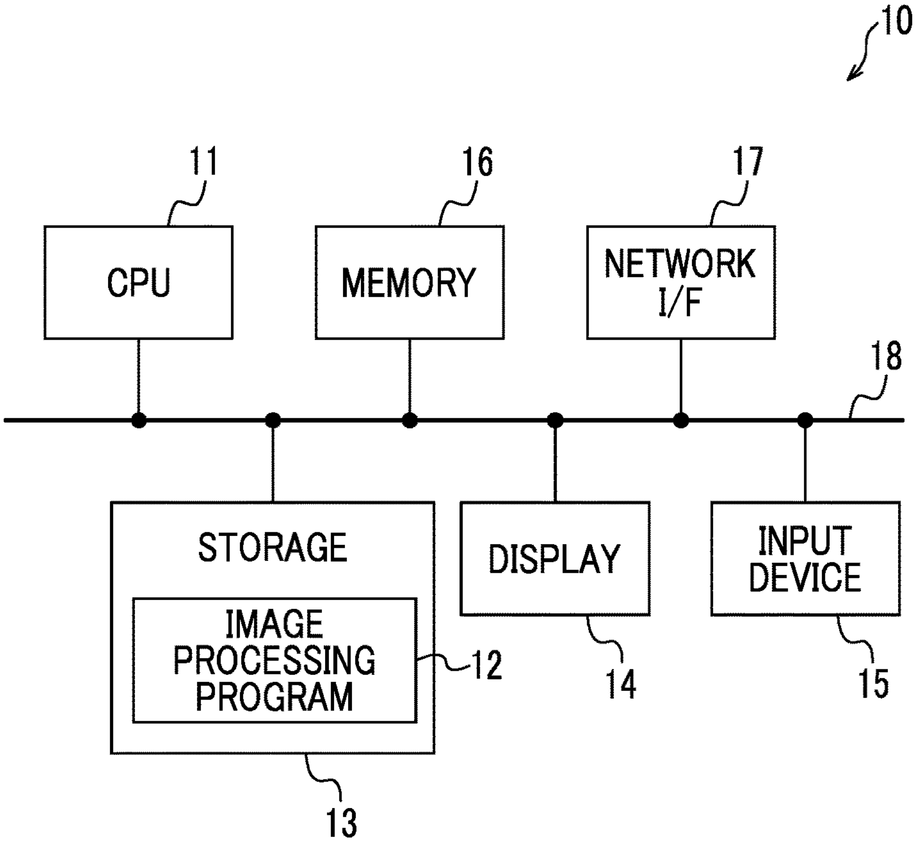
FIG. 6 is a diagram showing a schematic configuration of the image processing device according to the first embodiment.

Next, the image processing device according to the first embodiment will be described. FIG. 6 is a diagram showing a hardware configuration of the image processing device according to the present embodiment. As shown in FIG. 6, the image processing device 10 includes a central processing unit (CPU) 11, a non-volatile storage 13, and a memory 16 as a temporary storage region. In addition, the image processing device 10 includes a display 14 such as a liquid crystal display, an input device 15 such as a keyboard and a mouse, and a network interface (I/F) 17 connected to the network 5. The CPU 11, the storage 13, the display 14, the input device 15, the memory 16, and the network I/F 17 are connected to a bus 18. The CPU 11 is an example of the processor in the present disclosure.

The storage 13 is realized by, for example, a hard disk drive (HDD), a solid state drive (SSD), a flash memory, and the like. An image processing program 12 is stored in the storage 13 as a storage medium. The CPU 11 reads out the image processing program 12 from the storage 13, expands the image processing program 12 in the memory 16, and executes the expanded image processing program 12.

Figure 7:
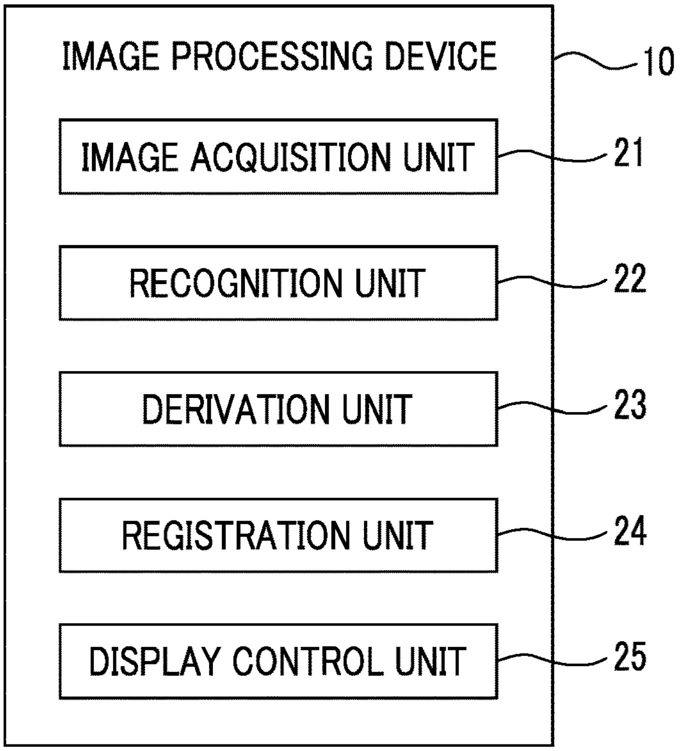
FIG. 7 is a functional configuration diagram of the image processing device according to the first embodiment.

Next, a functional configuration of the image processing device according to the first embodiment will be described. FIG. 7 is a diagram showing the functional configuration of the image processing device according to the first embodiment. As shown in FIG. 7, the image processing device 10 comprises an image acquisition unit 21, a recognition unit 22, a derivation unit 23, a registration unit 24, and a display control unit 25. Then, by executing the image processing program 12 by the CPU 11, the CPU 11 functions as the image acquisition unit 21, the recognition unit 22, the derivation unit 23, the registration unit 24, and the display control unit 25.

The image acquisition unit 21 sequentially acquires a plurality of fluoroscopic images T0 acquired by the fluoroscopic image pick-up device 3 during the treatment of the subject H at a predetermined frame rate. In addition, the image acquisition unit 21 sequentially acquires a plurality of ultrasound images corresponding to the plurality of fluoroscopic images T0 acquired by the ultrasonic endoscope device 6 at a predetermined frame rate. The ultrasound image acquired by the ultrasonic endoscope device 6 is an example of the two-dimensional ultrasound image of the present disclosure. In the following description, the ultrasound image means a two-dimensional ultrasound image unless otherwise noted.

Figure 5:
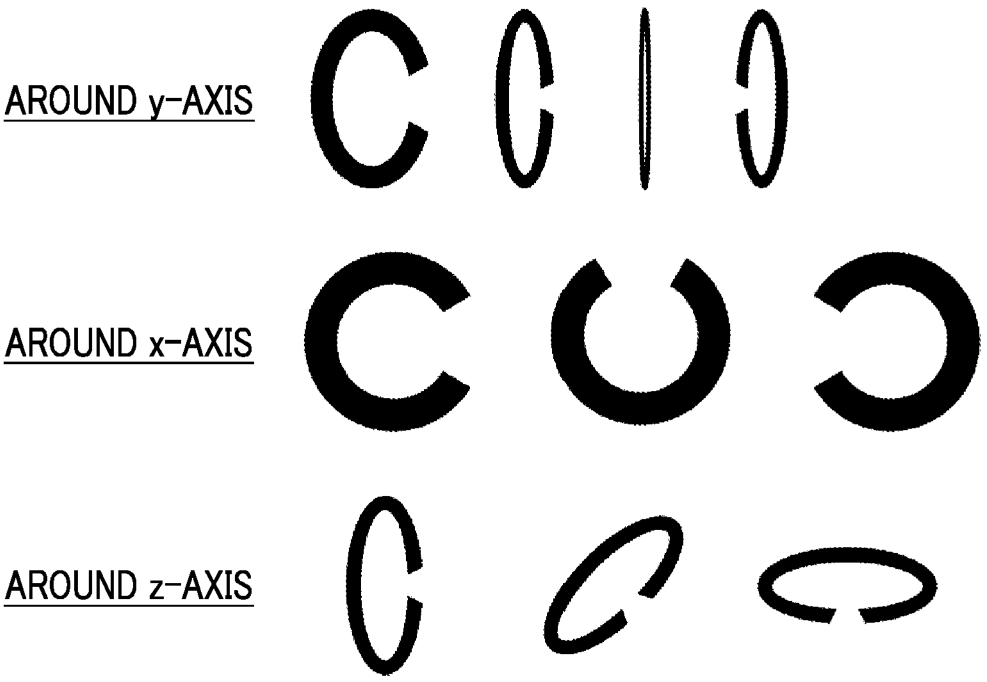
FIG. 5 is a diagram showing a change of an annular marker.

The recognition unit 22 recognizes the position and the posture of the endoscope 7 in the bronchus based on an image of the marker 8 (hereinafter, referred to as a marker image) included in the fluoroscopic image T0. Since the marker 8 is radiation-impermeable, the marker image appears as a region of high brightness (low density) in the fluoroscopic image T0. Therefore, the marker image can be detected from the fluoroscopic image T0 using threshold processing, a trained model, or the like. Here, based on the annular marker 8C as shown in FIGS. 3 to 5, it is possible to recognize the posture of the endoscope 7 based on the rotation around three axes in the subject. The position of the annular marker 8C in the fluoroscopic image T0 corresponds to the position of the distal end of the endoscope 7. A size of the marker 8 corresponds to the position of the endoscope 7 in a direction orthogonal to the fluoroscopic image T0, that is, in a depth direction.

The recognition unit 22 sets one of the fluoroscopic images T0 that are sequentially acquired, as a reference fluoroscopic image Tb, detects the marker image from the reference fluoroscopic image Tb, and recognizes a position and a posture of the marker image. The position and the posture of the marker image in the reference fluoroscopic image Tb are referred to as reference position and posture. The reference position need only be specified, for example, by the operator using the input device 15 to designate a first branch position of the bronchus, a position near the lesion, or the like.

After acquiring the reference fluoroscopic image Tb, the recognition unit 22 recognizes the position and the posture of the marker image in the fluoroscopic images T0 that are sequentially acquired. Thus, in the fluoroscopic images T0 that are sequentially acquired, the position and the posture of the endoscope 7 with reference to the reference position are sequentially recognized. The recognition unit 22 may recognize the position and the posture of the marker image by using the chess board marker 8B as an auxiliary in addition to the annular marker 8C.

Figure 8:
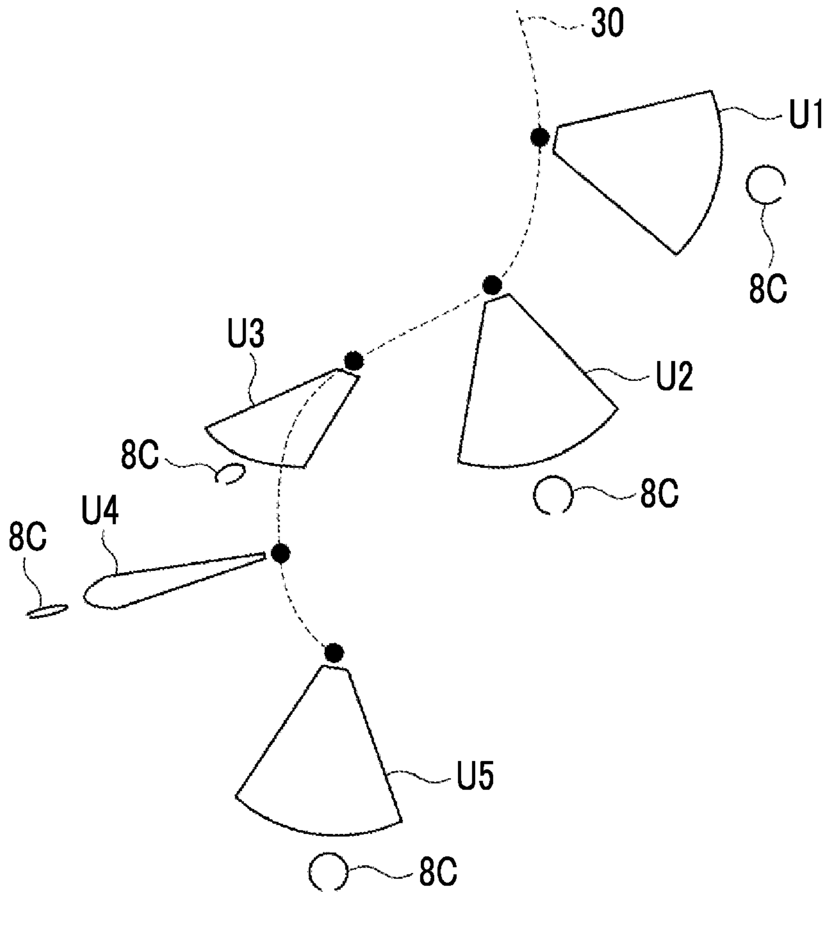
FIG. 8 is a diagram for describing derivation of a three-dimensional ultrasound image.

The derivation unit 23 derives a three-dimensional ultrasound image UV0 from the plurality of ultrasound images U0 based on the position and the posture of the endoscope 7 recognized for the plurality of fluoroscopic images T0. FIG. 8 is a diagram for describing the derivation of the three-dimensional ultrasound image UV0. In FIG. 8, a broken line indicates a route of movement of the endoscope 7 in the bronchus. FIG. 8 shows a state in which five ultrasound images U1 to U5 are acquired at predetermined time intervals in the route 30 along which the endoscope 7 has moved. Note that the route 20 of the endoscope in FIG. 8 is for the purpose of description and is different from the actual route. In addition, intervals between the ultrasound images U1 and U5 are also for the purpose of description and are different from the actual intervals. FIG. 8 shows the annular markers 8C included in fluoroscopic images T1 to T5 acquired in a case in which the respective ultrasound images U1 to U5 are acquired, in association with the ultrasound images U1 to U5.

As shown in FIG. 8, the position and the posture of the endoscope 7 change as the endoscope 7 advances in the bronchus along the route 30. Therefore, a position and an orientation of a cross section in the subject H represented by the ultrasound image change. The position and the orientation of the cross section represented by the ultrasound image correspond to the position and the orientation of the marker 8 included in the fluoroscopic image T0. Therefore, for two ultrasound images (U1 and U2) whose acquisition times are adjacent to each other, the derivation unit 23 derives a spatial positional relationship between corresponding pixels of the ultrasound image U1 and the ultrasound image U2 from the position and the posture of the endoscope 7 in a case in which the ultrasound image U1 is acquired and the position and the posture of the endoscope 7 in a case in which the ultrasound image U2 is acquired.

Figure 9:
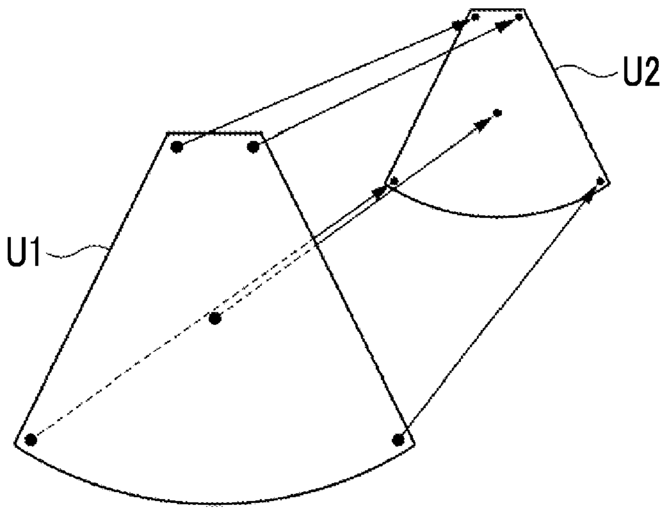
FIG. 9 is a diagram for describing derivation of a spatial positional relationship of corresponding pixels between ultrasound images.

FIG. 9 is a diagram for describing derivation of the spatial positional relationship of the corresponding pixels between the ultrasound images. As shown in FIG. 9, the derivation unit 23 derives, as the positional relationship, which spatial position in the ultrasound image U2 the position of each pixel in the ultrasound image U1 has moved to, based on the position and the posture of the endoscope 7 that have changed between acquisition of the ultrasound image U1 and acquisition of the ultrasound image U2. In FIG. 9, changes in five pixels in the ultrasound image U1 are shown by a vector from the ultrasound image U1 to the ultrasound image U2.

Figure 10:
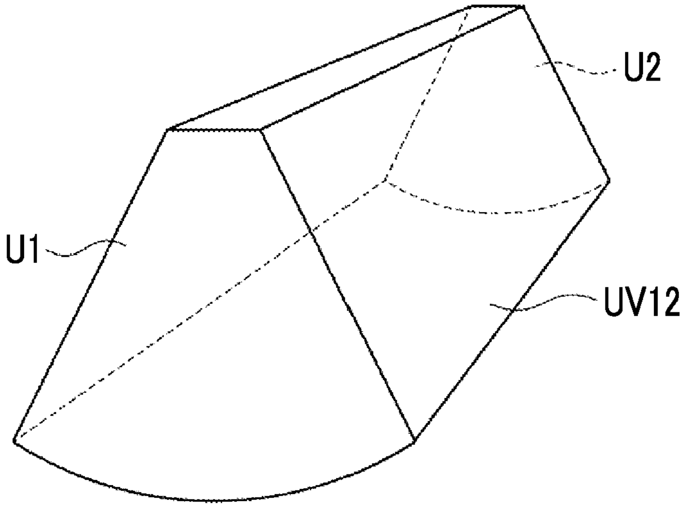
FIG. 10 is a diagram for describing the derivation of the three-dimensional ultrasound image.

Then, the derivation unit 23 derives a three-dimensional ultrasound image UV12, as shown in FIG. 10, by interpolating the corresponding pixels of the ultrasound image U1 and the ultrasound image U2 based on the derived positional relationship.

The derivation unit 23 derives a three-dimensional ultrasound image UV0 by repeating the above-described processing for the ultrasound images whose acquisition times are adjacent to each other.

The registration unit 24 performs registration between the three-dimensional ultrasound image UV0 derived by the derivation unit 23 and the fluoroscopic image T0. Therefore, the registration unit 24 projects the three-dimensional ultrasound image UV0 derived from the ultrasound images U0 acquired so far in an imaging direction of the latest fluoroscopic image T0 to obtain a two-dimensional projection ultrasound image UT0. As a projection method, any projection method such as maximum value projection or minimum value projection can be used.

Then, the registration unit 24 performs registration between the two-dimensional projection ultrasound image UT0 and the fluoroscopic image T0. For the registration, any method such as rigid body registration or non-rigid body registration can be used.

Figure 11:
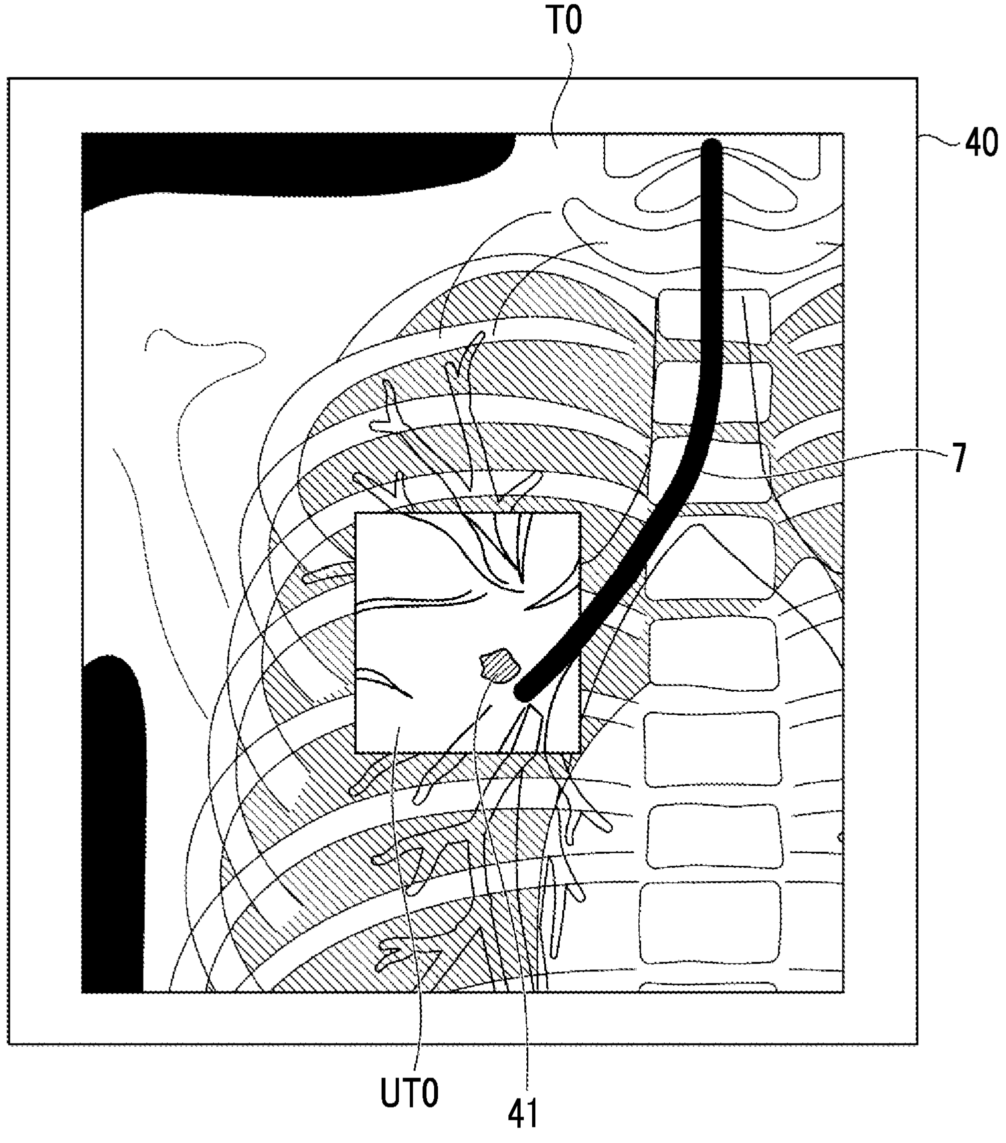
FIG. 11 is a diagram showing a display screen.

The display control unit 25 superimposes the registered two-dimensional projection ultrasound image UT0 on the fluoroscopic image T0 and displays the superimposed image on the display 14. FIG. 11 is a diagram showing a display screen. As shown in FIG. 11, the fluoroscopic image T0 is displayed on the display screen 40. The fluoroscopic image T0 includes an image of the endoscope 7. The two-dimensional projection ultrasound image UT0 is superimposed and displayed in the vicinity of the distal end of the endoscope 7 in the fluoroscopic image T0. In addition, it can be seen that the lesion 41 is included in the two-dimensional projection ultrasound image UT0.

Figure 12:
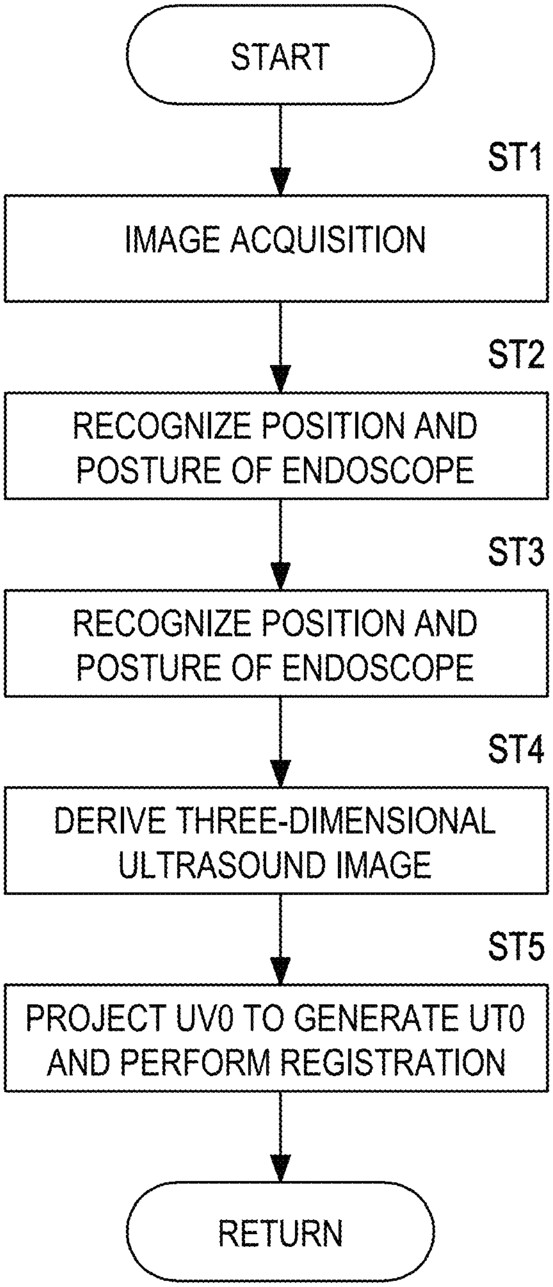
FIG. 12 is a flowchart showing a process performed in the first embodiment.

Next, a process performed in the first embodiment will be described. FIG. 12 is a flowchart showing the process performed in the first embodiment. First, the image acquisition unit 21 acquires the fluoroscopic image T0 and the ultrasound image U0 (image acquisition: step ST1). Next, the recognition unit 22 recognizes the position and the posture of the endoscope 7 in the bronchus based on the marker image included in the fluoroscopic image T0 (step ST2). Subsequently, the derivation unit 23 derives the three-dimensional ultrasound image UV0 from the plurality of ultrasound images U0 based on the position and the posture of the endoscope 7 recognized for the plurality of fluoroscopic images T0 (step ST3).

Then, the registration unit 24 performs registration between the three-dimensional ultrasound image UV0 and the latest fluoroscopic image T0 (step ST4), and the display control unit 25 superimposes and displays, on the fluoroscopic image T0, the registered three-dimensional ultrasound image UV0, that is, the two-dimensional projection ultrasound image UT0 (step ST5), and returns to step ST1.

As described above, in the present embodiment, the three-dimensional ultrasound image UV0 is derived from the plurality of ultrasound images U0 based on the position and the posture of the endoscope 7 recognized for the plurality of fluoroscopic images T0. By using such a three-dimensional ultrasound image UV0, the position of the lesion included in the fluoroscopic image T0 can be easily confirmed.

In particular, by superimposing and displaying the three-dimensional ultrasound image UV0 on the fluoroscopic image T0, a positional relationship between the distal end of the endoscope 7 included in the fluoroscopic image T0 and the lesion included in the three-dimensional ultrasound image UV0 can be easily grasped. Therefore, in a case in which the tissue of the lesion is collected for a biopsy, an accuracy of collecting the tissue from the lesion can be improved based on the positional relationship between the distal end of the endoscope 7 included in the fluoroscopic image T0 and the lesion included in the three-dimensional ultrasound image UV0.

Figure 13:
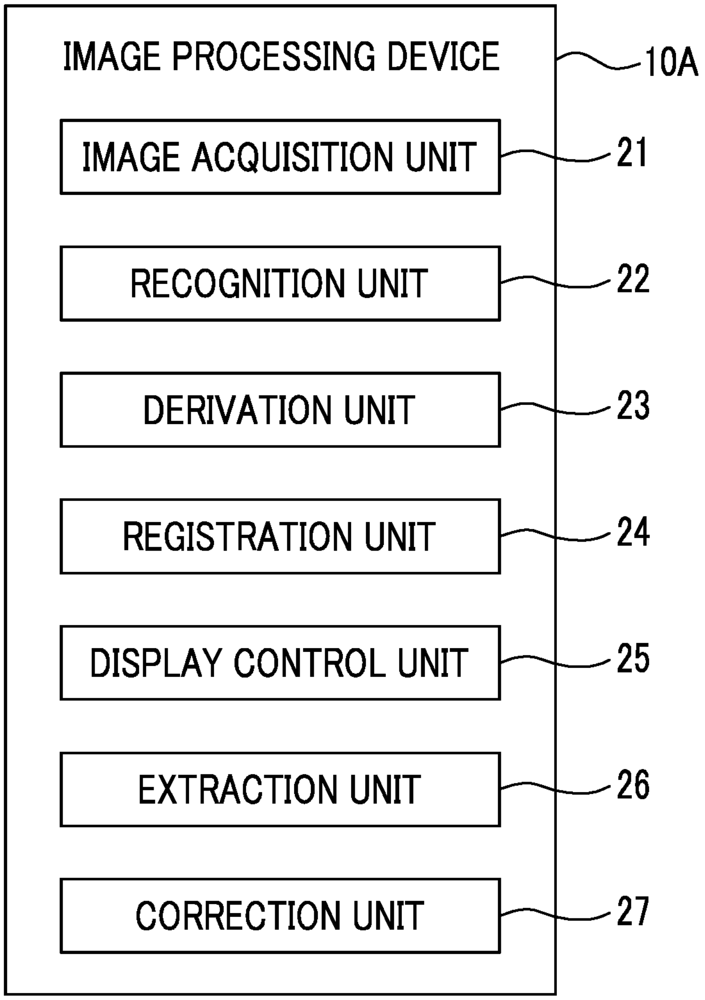
FIG. 13 is a functional configuration diagram of an image processing device according to a second embodiment.

Next, a second embodiment of the present disclosure will be described. FIG. 13 is a diagram showing a functional configuration of an image processing device according to the second embodiment of the present disclosure. In addition, in FIG. 13, the same components as those in FIG. 7 are denoted by the same reference numerals, and the detailed description thereof will not be repeated. As illustrated in FIG. 13, an image processing device 10A according to the second embodiment is different from the first embodiment in that the image processing device 10A further comprises an extraction unit 26 and a correction unit 27.

In the second embodiment, the image acquisition unit 21 acquires a three-dimensional image V0 of the subject H from the image storage server 4 in response to an instruction from the input device 15 by the operator before a treatment.

The extraction unit 26 extracts a body cavity into which the endoscope 7 is inserted from the three-dimensional image V0. In the second embodiment, since the endoscope 7 is inserted into the bronchus, the extraction unit 26 extracts the bronchus from the three-dimensional image V0. Therefore, the extraction unit 26 extracts a lung region from the three-dimensional image V0. As a method of extracting the lung region, any method, such as a method of extracting the lung region by creating a histogram of a signal value for each pixel in the three-dimensional image V0 and performing threshold processing for the lung or a region growing method based on a seed point indicating the lung, can be used. Note that a discriminator which has been subjected to machine learning to extract the lung region may be used.

Then, the extraction unit 26 extracts a graph structure of a bronchial region included in the lung region extracted from the three-dimensional image V0, as a three-dimensional bronchial region. As a method of extracting the bronchial region, for example, the method disclosed in JP2010-220742A can be used in which the graph structure of the bronchus is extracted using a Hessian matrix, the extracted graph structure is classified into a starting point, an end point, a branch point, and sides, and the starting point, the end point, and the branch point are connected with the sides to extract the bronchial region. Note that the method of extracting the bronchial region is not limited thereto.

The correction unit 27 corrects the position and the posture of the endoscope 7 according to a shape of the extracted bronchus. Therefore, the correction unit 27 performs a process of matching a coordinate system of the three-dimensional image V0 with a coordinate system of a distal end position of the endoscope 7. For example, the coordinate system of the three-dimensional image V0 is matched with the coordinate system of the distal end position of the endoscope 7 by performing coordinate transformation of the coordinate (three-dimensional) of the distal end position of the endoscope 7 such that the coordinate system of the endoscope 7 is matched with the coordinate system of the three-dimensional image V0.

Then, the correction unit 27 determines whether or not the distal end position of the endoscope 7 is in the bronchus, and corrects the recognized position and posture of the endoscope 7 such that the distal end position of the endoscope 7 is located in the bronchus in a case in which the distal end position of the endoscope 7 is not in the bronchus. On the other hand, the correction unit 27 does not correct the position and the posture of the endoscope 7 in a case in which the distal end position of the endoscope 7 is in the bronchus.

In a case in which the position and the posture of the endoscope 7 are corrected, the derivation unit 23 derives the three-dimensional ultrasound image UV0 based on the corrected position and posture of the endoscope. In a case in which the position and the posture of the endoscope 7 are not corrected, the derivation unit 23 derives the three-dimensional ultrasound image UV0 based on the position and the posture of the endoscope recognized by the recognition unit 22.

Figure 14:
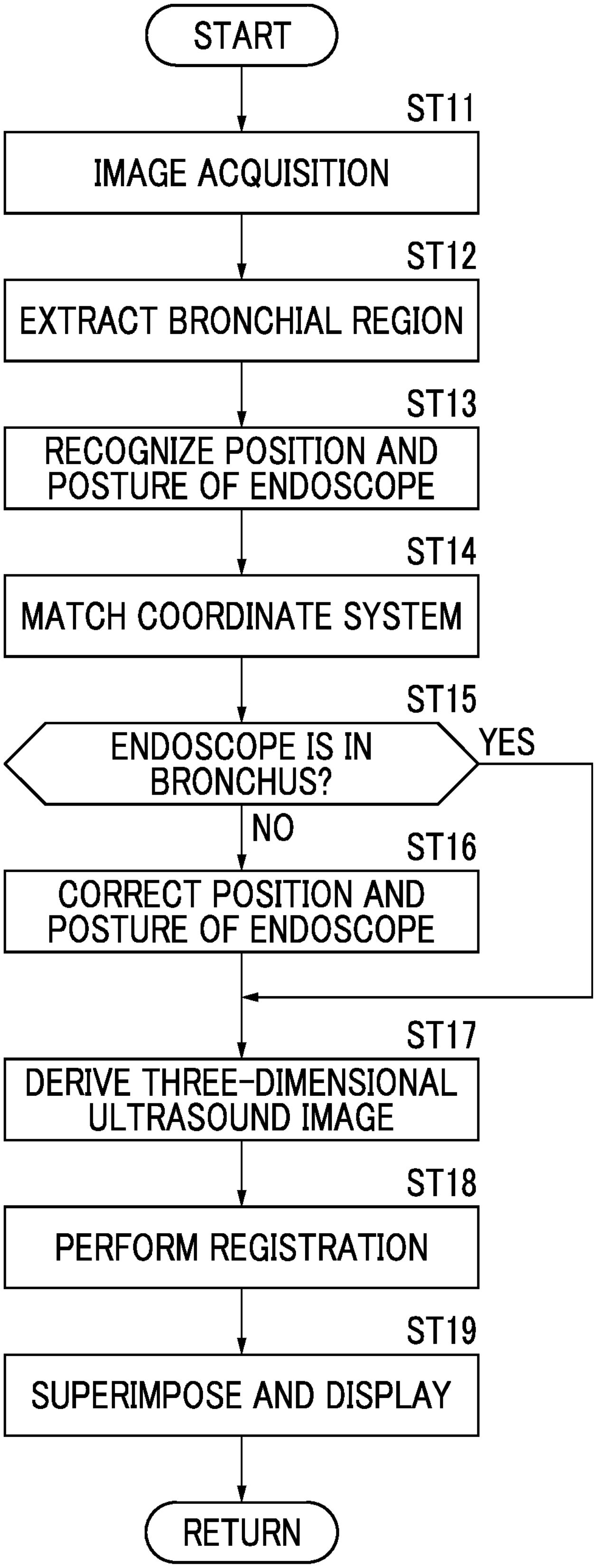
FIG. 14 is a flowchart showing a process performed in the second embodiment.

Next, a process performed in the second embodiment will be described. FIG. 14 is a flowchart showing the process performed in the second embodiment. First, the image acquisition unit 21 acquires the three-dimensional image V0, in addition to the fluoroscopic image T0 and the ultrasound image U0 (image acquisition: step ST11). Then, the extraction unit 26 extracts a bronchial region from the three-dimensional image V0 (step ST12). Next, the recognition unit 22 recognizes the position and the posture of the endoscope 7 in the bronchus based on the marker image included in the fluoroscopic image T0 (step ST13). Subsequently, the correction unit 27 performs a process of matching a coordinate system of the three-dimensional image V0 with a coordinate system of the position of the endoscope (step ST14), and determines whether or not the distal end position of the endoscope 7 is in the bronchus (step ST15).

In a case in which negative determination is made in step ST15, the correction unit 27 corrects the recognized position and posture of the endoscope 7 (step ST16). Subsequently, the derivation unit 23 derives the three-dimensional ultrasound image UV0 from the plurality of ultrasound images U0 based on the position and the posture of the endoscope 7 corrected for the plurality of fluoroscopic images T0 (step ST17).

In a case in which positive determination is made in step ST15, the process proceeds to step ST17, and the derivation unit 23 derives the three-dimensional ultrasound image UV0 from the plurality of ultrasound images U0 based on the position and the posture of the endoscope 7 recognized for the plurality of fluoroscopic images T0.

Then, the registration unit 24 performs registration between the three-dimensional ultrasound image UV0 and the latest fluoroscopic image T0 (step ST18), and the display control unit 25 superimposes and displays, on the fluoroscopic image T0, the registered three-dimensional ultrasound image UV0, that is, the two-dimensional projection ultrasound image UT0 (step ST19), and returns to step ST11.

As described above, in the second embodiment, the position and the posture of the endoscope are corrected in a case in which the position of the endoscope is not in the bronchus, so that an accuracy of recognition of the position of the endoscope can be improved. Therefore, the positional relationship between the distal end of the endoscope 7 included in the fluoroscopic image T0 and the lesion included in the three-dimensional ultrasound image UV0 can be accurately grasped, and as a result, the accuracy of collecting the tissue from the lesion can be improved.

Figure 15:
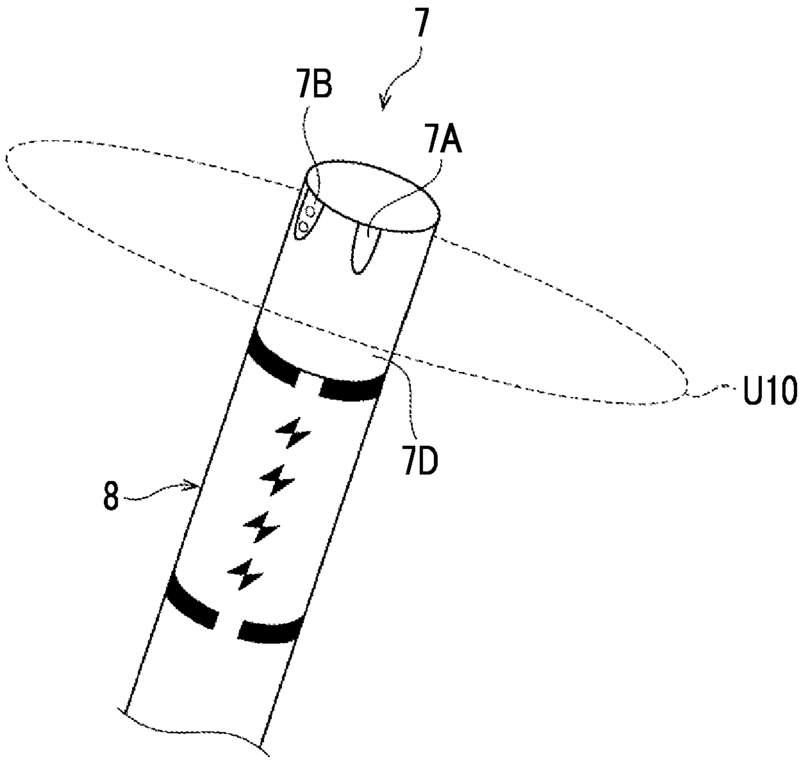
FIG. 15 is a diagram showing another example of the distal end portion of the endoscope according to the present embodiment.

In each of the above-described embodiments, as shown in FIG. 15, an endoscope having an ultrasound probe 7D capable of picking up an ultrasound image over the entire circumference may be used. In a case in which the endoscope 7 having such an ultrasound probe 7D is used, a circular ultrasound image U10 is acquired as shown in FIG. 15. This leads to derivation of the three-dimensional ultrasound image UV0, which has a three-dimensional shape like a deformed cylinder.

In addition, in each of the above-described embodiments, the processing in a case in which the lesion of the lung is collected by using a bronchial endoscope is described, but the present disclosure is not limited thereto. For example, the image processing device according to the present embodiment can also be applied in a case where an ultrasonic endoscope is inserted into a digestive organ such as a stomach to perform a biopsy of a tissue such as a pancreas or a liver.

In addition, in each of the above-described embodiments, for example, as a hardware structure of a processing unit that executes various types of processing such as the image acquisition unit 21, the recognition unit 22, the derivation unit 23, the registration unit 24, the display control unit 25, the extraction unit 26, and the correction unit 27, various types of processors shown below can be used. The various types of processors include, as described above, a CPU which is a general-purpose processor that executes software (program) to function as various types of processing units, as well as a programmable logic device (PLD) which is a processor having a circuit configuration that can be changed after manufacturing such as a field programmable gate array (FPGA), a dedicated electrical circuit which is a processor having a circuit configuration exclusively designed to execute specific processing such as an application specific integrated circuit (ASIC), and the like.

One processing unit may be configured of one of the various types of processors, or a combination of two or more processors of the same type or different types (for example, a combination of a plurality of FPGAs, or a combination of a CPU and an FPGA). Further, a plurality of processing units may be configured of one processor.

As an example of configuring a plurality of processing units with one processor, first, there is a form in which, as typified by computers such as a client and a server, one processor is configured by combining one or more CPUs and software, and the processor functions as a plurality of processing units. Second, there is a form in which, as typified by a system on chip (SoC) and the like, in which a processor that implements functions of an entire system including a plurality of processing units with one integrated circuit (IC) chip is used. As described above, the various types of processing units are configured using one or more of the various types of processors as a hardware structure.

Furthermore, as the hardware structure of the various types of processors, more specifically, an electric circuit (circuitry) in which circuit elements such as semiconductor elements are combined can be used.

What is claimed is:

1. An endoscope system, comprising:

a fluoroscopic image pick-up device comprising an X-ray source and an X-ray collector, capturing a plurality of radiation images;

an ultrasonic endoscope, comprising an ultrasonic imaging device and a marker which is radiation impermeable, capturing a plurality of two-dimensional ultrasound images corresponding to the plurality of radiation images; and an image processing device comprising:

at least one processor, wherein the at least one processor is configured to:

sequentially acquire the plurality of radiation images of a subject in a body cavity into which an ultrasonic endoscope is inserted, wherein the plurality of radiation images comprise an image of the ultrasonic endoscope;

sequentially acquire the plurality of two-dimensional ultrasound images corresponding to the plurality of radiation images, which are captured by the ultrasonic endoscope, wherein each of the plurality of two-dimensional ultrasound images includes a target region;

perform an image processing on the plurality of radiation images to recognize a position and a posture of the ultrasonic endoscope in the body cavity based on a position and a shape of the marker in each of the plurality of radiation images;

generate a three-dimensional ultrasound image from the plurality of two-dimensional ultrasound images including a first two-dimensional ultrasound image and a second two-dimensional ultrasound image based on the position and the posture of the ultrasonic endoscope recognized from the plurality of radiation images, wherein the at least one processor derives a vector representing a positional relationship between the first two-dimensional ultrasound image and the second two-dimensional ultrasound image based on the position and the posture of the ultrasonic endoscope, and interpolates corresponding pixels of the first two-dimensional ultrasound image and the second two-dimensional ultrasound image based on the vector representing the positional relationship to generate the three-dimensional ultrasound image;

project the three-dimensional ultrasound image to obtain a two-dimensional projection ultrasound image;

superimpose the two-dimensional projection ultrasound image which includes an image of the target region on the radiation image which includes the image of the ultrasonic endoscope to generate a superimposed image, wherein the superimposed image indicates a distance between the image of the ultrasonic endoscope included in the radiation image and the image of the target region included in the two-dimensional projection ultrasound image; and display, on a display screen of the image processing device, the superimposed image.

2. The endoscope system according to claim 1, wherein the at least one processor is configured to:

extract the body cavity from a three-dimensional image of the subject acquired, by a three-dimensional image pick-up device, in advance, wherein the three-dimensional image pick-up device comprises a computed tomography (CT) device, a magnetic resonance imaging (MRI) device or a positron emission tomography (PET) device;

correct the position and the posture of the ultrasonic endoscope according to a shape of the extracted body cavity; and derive the three-dimensional ultrasound image from the plurality of two-dimensional ultrasound images based on the corrected position and posture.

3. An image processing method comprising:

sequentially acquiring a plurality of radiation images of a subject having a body cavity into which an ultrasonic endoscope is inserted, wherein a plurality of two-dimensional ultrasound images corresponding to the plurality of radiation images are captured by the ultrasonic endoscope comprising an ultrasonic imaging device and a marker which is radiation impermeable, the plurality of radiation images are captured by a fluoroscopic image pick-up device comprising an X-ray source and an X-ray collector, and the plurality of radiation images comprise an image of the ultrasonic endoscope;

sequentially acquiring the plurality of two-dimensional ultrasound images corresponding to the plurality of radiation images, which are captured by the ultrasonic endoscope, wherein each of the plurality of two-dimensional ultrasound images includes a target region;

performing an image processing on the plurality of radiation images to a position and a posture of the ultrasonic endoscope in the body cavity based on a position and a shape of the marker in each of the plurality of radiation images;

generating a three-dimensional ultrasound image from the plurality of two-dimensional ultrasound images including a first two-dimensional ultrasound image and a second two-dimensional ultrasound image based on the position and the posture of the ultrasonic endoscope recognized from the plurality of radiation images, wherein a vector representing a positional relationship between the first two-dimensional ultrasound image and the second two-dimensional ultrasound image based on the position and the posture of the ultrasonic endoscope are derived, and corresponding pixels of the first two-dimensional ultrasound image and the second two-dimensional ultrasound image based on the vector representing the positional relationship are interpolated to generate the three-dimensional ultrasound image;

projecting the three-dimensional ultrasound image to obtain a two-dimensional projection ultrasound image;

superimposing the two-dimensional projection ultrasound image which includes an image of the target region on the radiation image which includes the image of the ultrasonic endoscope to generate a superimposed image, wherein the superimposed image indicates a distance between the image of the ultrasonic endoscope included in the radiation image and the image of the target region included in the two-dimensional projection ultrasound image; and displaying the superimposed image.

4. A non-transitory computer-readable storage medium that stores an image processing program causing a computer to execute a process comprising:

sequentially acquire a plurality of radiation images of a subject in a body cavity into which an ultrasonic endoscope is inserted, wherein a plurality of two-dimensional ultrasound images corresponding to the plurality of radiation images are captured by the ultrasonic endoscope comprising an ultrasonic imaging device and a marker which is radiation impermeable, the plurality of radiation images are captured by a fluoroscopic image pick-up device comprising an X-ray source and an X-ray collector, and the plurality of radiation images comprise an image of the ultrasonic endoscope;

sequentially acquiring the plurality of two-dimensional ultrasound images corresponding to the plurality of radiation images, which are captured by the ultrasonic endoscope, wherein each of the plurality of two-dimensional ultrasound images includes a target region;

performing an image processing on the plurality of radiation images to a position and a posture of the ultrasonic endoscope in the body cavity based on a position and a shape of the marker in each of the plurality of radiation images;

generating a three-dimensional ultrasound image from the plurality of two-dimensional ultrasound images including a first two-dimensional ultrasound image and a second two-dimensional ultrasound image based on the position and the posture of the ultrasonic endoscope recognized from the plurality of radiation images, wherein a vector representing a positional relationship between the first two-dimensional ultrasound image and the second two-dimensional ultrasound image based on the position and the posture of the ultrasonic endoscope are derived, and corresponding pixels of the first two-dimensional ultrasound image and the second two-dimensional ultrasound image based on the vector representing the positional relationship are interpolated to generate the three-dimensional ultrasound image;

projecting the three-dimensional ultrasound image to obtain a two-dimensional projection ultrasound image;

superimposing the two-dimensional projection ultrasound image which includes an image of the target region on the radiation image which includes the image of the ultrasonic endoscope to generate a superimposed image, wherein the superimposed image indicates a distance between the image of the ultrasonic endoscope included in the radiation image and the image of the target region included in the two-dimensional projection ultrasound image; and displaying the superimposed image.

* * * * *